(12) United States Patent
Lendvai et al.

(10) Patent No.: US 8,188,149 B2
(45) Date of Patent: May 29, 2012

(54) USE OF R(+)-N-PROPARGY1-1-AMINOINDAN TO TREAT OR PREVENT HEARING LOSS

(75) Inventors: Balazs Lendvai, Budapest (HU); Vizi E. Szilveszter, Budapest (HU); Zelles Tibor, Budapest (HU); Halmos Gyorgy, Groningen (NL)

(73) Assignee: Teva Pharmaceutical Industries, Ltd., Petach-Tikva (IE)

( * ) Notice: Subject to any disclaimer, the term of this patent is extended or adjusted under 35 U.S.C. 154(b) by 0 days.

(21) Appl. No.: 12/283,946

(22) Filed: Sep. 16, 2008

(65) Prior Publication Data

US 2009/0076160 A1 Mar. 19, 2009

Related U.S. Application Data

(60) Provisional application No. 60/994,222, filed on Sep. 17, 2007.

(51) Int. Cl.
*A01N 33/02* (2006.01)
*A01N 37/12* (2006.01)
*A01N 37/44* (2006.01)
*A61K 31/135* (2006.01)
*A61K 31/195* (2006.01)

(52) U.S. Cl. ........................................ 514/647; 514/567
(58) Field of Classification Search .................. 514/647, 514/567
See application file for complete search history.

(56) References Cited

U.S. PATENT DOCUMENTS

| | | | |
|---|---|---|---|
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,630,514 B2 | 10/2003 | Youdim et al. |
| 6,635,667 B2 | 10/2003 | Thomas |
| 6,956,060 B2 | 10/2005 | Youdim et al. |
| 7,396,860 B2 | 7/2008 | Blaugrund et al. |
| 7,491,847 B2 | 2/2009 | Frenkel |
| 7,547,806 B2 | 6/2009 | Frenkel et al. |
| 7,572,834 B1 | 8/2009 | Sterling et al. |
| 7,598,420 B1 | 10/2009 | Sterling et al. |
| 7,619,117 B1 | 11/2009 | Sterling et al. |
| 7,750,051 B2 | 7/2010 | Frenkel et al. |
| 7,815,942 B2 | 10/2010 | Peskin |
| 7,855,233 B2 | 12/2010 | Frenkel et al. |
| 2006/0018957 A1 | 1/2006 | Lerner et al. |
| 2006/0094783 A1* | 5/2006 | Youdim et al. ............... 514/554 |
| 2006/0188581 A1 | 8/2006 | Peskin |
| 2007/0021352 A1 | 1/2007 | Anderson et al. |
| 2007/0100001 A1 | 5/2007 | Youdim et al. |
| 2007/0112217 A1 | 5/2007 | Frenkel et al. |
| 2007/0232700 A1 | 10/2007 | Blaugrund et al. |
| 2008/0107729 A1* | 5/2008 | Amin et al. ................... 424/465 |
| 2008/0146676 A1 | 6/2008 | Frenkel et al. |
| 2008/0161408 A1 | 7/2008 | Frenkel et al. |
| 2009/0062400 A1 | 3/2009 | Oron et al. |
| 2009/0069230 A1* | 3/2009 | Pentyala et al. ............... 514/12 |
| 2009/0111892 A1 | 4/2009 | Patashnick et al. |
| 2009/0181086 A1 | 7/2009 | Safadi et al. |
| 2009/0312436 A1 | 12/2009 | Levy et al. |
| 2009/0318564 A1 | 12/2009 | Frenkel et al. |
| 2010/0008983 A1 | 1/2010 | Safadi et al. |
| 2010/0010095 A1 | 1/2010 | Frenkel |
| 2010/0010098 A1 | 1/2010 | Elffrink |
| 2010/0029987 A1 | 2/2010 | Allegrini et al. |
| 2010/0137447 A1 | 6/2010 | Lehmann et al. |
| 2010/0144887 A1 | 6/2010 | Frenkel et al. |
| 2010/0145101 A1 | 6/2010 | Frenkel et al. |
| 2010/0168239 A1 | 7/2010 | Poewe |
| 2010/0189787 A1 | 7/2010 | Safadi et al. |
| 2010/0189788 A1 | 7/2010 | Safadi et al. |
| 2010/0189790 A1 | 7/2010 | Safadi et al. |
| 2010/0189791 A1 | 7/2010 | Safadi et al. |
| 2010/0234636 A1 | 9/2010 | Stahl |

FOREIGN PATENT DOCUMENTS

| | | |
|---|---|---|
| WO | WO 2008/019871 | 2/2008 |
| WO | WO 2008/131961 | 11/2008 |
| WO | WO 2009/081148 | 7/2009 |
| WO | WO 2009/122301 | 10/2009 |
| WO | WO 2009/152777 | 12/2009 |
| WO | WO 2010/007181 | 1/2010 |
| WO | WO 2010/013048 | 2/2010 |
| WO | WO 2010/049379 | 5/2010 |
| WO | WO 2010/070090 | 6/2010 |

(Continued)

OTHER PUBLICATIONS

Bergemalm, P. Acta Oto-larngologica, 2003, vol. 123, pp. 836-845.*

(Continued)

*Primary Examiner* — Samira Jean-Louis

(74) *Attorney, Agent, or Firm* — John P. White; Cooper & Dunham LLP

(57) ABSTRACT

The subject invention provides a method of treating or inhibiting hearing loss in a mammalian subject. The method includes administering to a mammalian subject an amount of R(+)-N-propargyl-1-aminoindan or pharmaceutically acceptable salt thereof effective to treat or inhibit the hearing loss in the subject.

17 Claims, 4 Drawing Sheets

(2 of 4 Drawing Sheet(s) Filed in Color)

FOREIGN PATENT DOCUMENTS

| WO | WO 2011/003938 | 1/2011 |
|----|----------------|--------|
| WO | WO 2011/009873 | 1/2011 |
| WO | WO 2011/010324 | 1/2011 |

OTHER PUBLICATIONS

Vasquez et al. Ear, Nose and Throat Journal, Mar. 2003, vol. 82, No. 3, pp. 181-184.*
Huang et al. European Journal of Pharmacology, 1999, vol. 366, pp. 127-135.*
U.S. Appl. No. 11/791,684, filed May 24, 2007, Patashnik et al.
U.S. Appl. No. 12/223,794, filed Aug. 7, 2008, Poewe.
U.S. Appl. No. 12/231,601, filed Sep. 3, 2008, Oron et al.
Office Action issued Sep. 29, 1993 in the U.S. Appl. No. 08/063,455.
Office Action issued May 18, 1993 in the U.S. Appl. No. 08/063,455.
Office Action issued Jul. 26, 1994 in the U.S. Appl. No. 08/255,046.
Office Action issued Nov. 2, 1994 in the U.S. Appl. No. 08/255,046.
Office Action issued Dec. 14, 1995 in the U.S. Appl. No. 08/459,402.
Office Action issued Jul. 3, 1996 in the U.S. Appl. No. 08/458,645.
Office Action issued Dec. 24, 1996 in the U.S. Appl. No. 08/466,250.
Office Action issued Jun. 27, 1996 in the U.S. Appl. No. 08/466,250.
Office Action issued Dec. 19, 1995 in the U.S. Appl. No. 08/466,069.
Office Action issued Apr. 5, 1996 in the U.S. Appl. No. 08/446,439.
Office Action issued Sep. 8, 2000 in the U.S. Appl. No. 08/952,705.
Aug. 26, 1996 International Search Report for International Application No. PCT/US96/07465.
Office Action issued Jul. 26, 2002 in the U.S. Appl. No. 10/016,268.
Office Action issued Sep. 12, 2006 in the U.S. Appl. No. 10/712,958.
Office Action issued Dec. 27, 2006 in the U.S. Appl. No. 10/712,958.
Office Action issued Aug. 27, 2007 in the U.S. Appl. No. 10/712,958.
Jun. 16, 2004 International Search Report for International Application No. PCT/US03/36288.
Supplemental European Search Report for European Patent Application No. 03783422.3, issued Apr. 14, 2008.
Office Action issued May 1, 2009 in the U.S. Appl. No. 11/731,493.
Office Action issued Sep. 17, 2009 in the U.S. Appl. No. 11/731,493.
Oct. 28, 2008 Intl. Preliminary Report on Patentability and the Written Opinion of the International Searching Authority for International Application No. PCT/US07/08261.
Aug. 28, 2008 International Search Report for PCT International Application No. PCT/US07/08261.
Extended European Search Report of European Application No. EP 07754738.8, issued Jun. 3, 2009.
Official Action issued in European Application No. EP 07754738.8, issued Sep. 17, 2009.
Dec. 12, 2008 International Search Report for International Application No. PCT/US2008/10365.
Office Action issued Oct. 25, 2007 in the U.S. Appl. No. 11/595,726.
U.S. Appl. No. 12/223,794, filed Aug. 7, 2008.
Sep. 24, 2008 International Search Report for International Application No. PCT/US07/04884.
Oct. 14, 2008 Intl. Preliminary Report on Patentability and the Written Opinion of the International Searching Authority for International Application No. PCT/US07/04884.
U.S. Appl. No. 12/456,166, filed Aug. 7, 2008.
Aug. 5, 2009 International Search Report for International Application No. PCT/US09/03528.
U.S. Appl. No. 12/456,642, filed Jun. 19, 2009.

U.S. Appl. No. 12/456,643, filed Jun. 19, 2009.
U.S. Appl. No. 12/456,029, filed Jun. 9, 2009.
U.S. Appl. No. 12/456,031, filed Jun. 9, 2009.
U.S. Appl. No. 12/455,976, filed Jun. 9, 2009.
U.S. Appl. No. 12/456,001, filed Jun. 9, 2009.
U.S. Appl. No. 12/283,107, filed Sep. 8, 2008.
U.S. Appl. No. 12/455,969, filed Jun. 10, 2009.
Dec. 3, 2008 International Search Report for PCT International Application No. PCT/US08/10836.
Youdim MBH, et al., "Rasagiline (N-propargyl-1R(+)-aminoindan), a selective and potent inhibitor of mitochondrial monoamine oxidase B", Br. J. Pharmacol., 2001,132:500-506.
Blandini, F. et al. (2004) Neuroprotective effect of rasagiline in a rodent model of Parkinson's disease. Exp Neurol. Jun. 2004;187(2):455-459.
Waibel S. et al. (2004) Rasagiline alone and in combination with riluzole prolongs survival in an ALS mouse model. 251 (9) 1080-1084.
Bar-am et al. (2004) Regulation of protein kinase C by the anti-Parkinson drug, MAO-B inhibitor, rasagiline and its derivatives . . . Journal of Neurochemistry 89 (5),1119-1125.
Youdim MBH and Weistock M. (2001) Molecular Basis of Neuroprotective Activities of Rasagiline and the Anti-Alzheimer Drug . . . Cell. Mol. Neurobio. 21(6) 555-573.
Akao Y. et al. (2002) Mitochondrial permeability transition mediates apoptosis induced by N-methyl(R)salsolinol, an endogenous neurotoxin . . . 82 (4) 913-923.
Youdim MBH et al. (2003) The essentiality of Bcl-2, PKC and proteasome-ubiquitin complex activations in the neuroprotective-antiapoptotic . . . Biochem Pharmacol. 66(8):1635-1641.
Weinreb O. et al. (2004) Neurological mechanisms of green tea polyphenols in Alzheimer's and . . . The Journal of Nutritional Biochemistry, vol. 15, Issue 9, pp. 506-516.
Speiser Z, et al., "Studies with rasagiline, a monamine oxidase-B inhibitor, in experimental focal ischemia in the rat" J. Neural Transm., 1999, 106:593-606.
Finberg JP, Youdim MB, (2002) Pharmacological properties of the anti-Parkinson drug rasagiline; modification of endogenous brain amines . . . Neuropharmacology 43(7):1110-1118.
Puel J-L, (1995) Chemical synaptic transmission in the cochlea. Prog Neurobiol 47: 449-476.
Eybalin M, (1993) Neurotransmitters and neuromodulators of the mammalian cochlea. Physiol Rev 73: 309-373.
Yogev-Falach et al. (2003) Amyloid Processing and Signal Transduction Properties of Antiparkinson-Antialzheimer . . . Annals of the New York Academy of Sciences 993:378-386.
Youdim MBH et al. (2003) Neuroprotective Strategies in Parkinson's Disease: An Update on Progress. CNS Drugs. 17(10):729-762.
Parkinson Study Group (2004), "A Controlled, Randomized, Delayed-Start Study of Rasagiline in Early Parkinson's Disease", Arch. Neurol., 61(4):561-6.
Mar. 24, 2010 International Prelim. Report on Patentability and the Written Opinion of the International Searching Authority for International Application No. PCT/US08/10836.
Eybalin M, Pujol R, (1989) Cochlear neuroactive substances. Arch Otorhinolaryngol 246: 228-234.
U.S. Appl. No. 12/901,281, filed Oct. 8, 2010 (Lorenzl).
U.S. Appl. No. 12/974,769, filed Dec. 21, 2010 (Frenkel et al.).

* cited by examiner

USE OF R(+)-N-PROPARGY1-1-AMINOINDAN TO TREAT OR PREVENT HEARING LOSS

This application claims the benefit of U.S. Provisional Application No. 60/994,222, filed Sep. 17, 2007, the entire content of which is hereby incorporated by reference herein.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Hearing loss is a serious handicap which affects millions of people. Hearing impairments can be attributed to a wide variety of causes, including infections, mechanical injury, loud sounds, aging, and chemical-induced ototoxicity that damages neurons and/or hair cells of the peripheral auditory system.

The peripheral auditory system consists of auditory receptors, hair cells in the organ of Corti, and primary auditory neurons, the spiral ganglion neurons in the cochlea. The activity of the synapse between the inner hair cells (IHCs) and the type II afferent dendrites is modulated by the lateral olivocochlear (LOC) efferent fibers (Eybalin M, (1993) Neurotransmitters and neuromodulators of the mammalian cochlea. Physiol Rev 73: 309-373; Eybalin M, Pujol R, (1989) Cochlear neuroactive substances. Arch Otorhinolaryngol 246: 228-234; Puel J-L, (1995) Chemical synaptic transmission in the cochlea. Prog Neurobiol 47: 449-476).

Ototoxicity is caused by drugs or chemicals that damage the inner ear or the vestibulocochlear nerve, which sends balance and hearing information to the brain from the inner ear. Ototoxicity may result in temporary or permanent losses of hearing, balance, or both. Substances that may cause ototoxicity include antibiotics, chemotherapy drugs, environmental chemicals, loop diuretics, aspirin and quinine products.

Rasagiline, R(+)-N-propargyl-1-aminoindan, is a potent second generation monoamine oxidase (MAO) B inhibitor (Finberg J P, Youdim M B, (2002) Pharmacological properties of the anti-Parkinson drug rasagiline; modification of endogenous brain amines, reserpine reversal, serotonergic and dopaminergic behaviours. Neuropharmacology 43(7):1110-8). Rasagiline mesylate in a 1 mg tablet is commercially available as monotherapy or as an adjunct for the treatment of idiopathic Parkinson's disease as Azilect® from Teva Pharmaceuticals Industries, Ltd. (Petach Tikva, Israel) and H. Lundbeck A/S (Copenhagen, Denmark). See, e.g. AZILECT®, Physician's Desk Reference (2006), 60$^{th}$ Edition, Thomson Healthcare. Recent studies have demonstrated that, in addition to its MAO-B inhibitor activity, rasagiline possesses potent neuroprotective activity demonstrated by in vitro and in vivo experiments. Neuroprotection by rasagiline was achieved in animal models of closed head trauma (Huang W, Chen Y, Shohami E, Weinstock M. (1999) Neuroprotective effect of rasagiline, a selective monoamine oxidase-B inhibitor, against closed head injury in the mouse. Eur J. Pharmacol. 366(2-3):127-35), global focal ischemia (Speiser Z, Mayk A, Eliash S, Cohen S. (1999) Studies with rasagiline, a MAO-B inhibitor, in experimental focal ischemia in the rat. 106 (7-8) 593-606) and MPTP(1-methyl-4-phenyl-1,2,3,6-tetrahydropyridine)-induced neurotoxicity (Sage et al. 2001, 2003) as well as transgenic model of amyotrophic lateral sclerosis (Waibel S. et al. (2004) Rasagiline alone and in combination with riluzole prolongs survival in an ALS mouse model. 251 (9) 1080-1084) and 6-OHDA(6-hydroxydopamine) model of Parkinson's disease (Blandini, F. et al. (2004) Neuroprotective effect of rasagiline in a rodent model of Parkinson's disease. Exp Neurol. 2004 June; 187(2):455-9). Cell culture experiments have shown that rasagiline potently suppresses apoptotic cell death initiated by mitochondria (Youdim M B H, et al., (2001) Rasagiline (N-propargyl-1R (+)-aminoindan), a selective and potent inhibitor of mitochondrial monoamine oxidase B. Br. J. Pharmacol., 132:500-6; Akao Y. et al. (2002) Mitochondrial permeability transition mediates apoptosis induced by N-methyl(R)salsolinol, an endogenous neurotoxin, and is inhibited by Bcl-2 and rasagiline, N-propargyl-1(R)-aminoindan. 82 (4) 913-923) by preventing preapoptotic swelling of mitochondria, caspase 3 activation, activation of nuclear PARP(poly ADP ribose polymerase)-1, translocation of GADPH(glyceraldehydes-3-phosphate dehydroxenase), and nucleasomal DNA fragmentation (Youdim M B H and Weistock M. (2001) Molecular Basis of Neuroprotective Activities of Rasagiline and the Anti-Alzheimer Drug TV3326 [N-Propargyl-(3R) Aminoindan-5-YL)-Ethyl Methyl Carbamate]. Cell. Mol. Neurobio. 21(6) 555-573; Youdim M B H et al. (2003) Neuroprotective Strategies in Parkinson's Disease: An Update on Progress. CNS Drugs. 17(10):729-762; Bar-am et al. (2004) Regulation of protein kinase C by the anti-Parkinson drug, MAO-B inhibitor, rasagiline and its derivatives, in vivo. Journal of Neurochemistry 89 (5), 1119-1125; and Weinreb O. et al. (2004) Neurological mechanisms of green tea polyphenols in Alzheimer's and Parkinson's diseases. The Journal of Nutritional Biochemistry, Volume 15, Issue 9, Pages 506-516). Further, rasagiline induces increase of the anti-apoptotic Bcl-2 and Bcl-xL expression parallel to downregulation of proapoptotic Bad and Bax (Youdim M B H et al. (2003) The essentiality of Bcl-2, PKC and proteasome-ubiquitin complex activations in the neuroprotective-antiapoptotic action of the anti-Parkinson drug, rasagiline. Biochem Pharmacol. 66(8):1635-41; Yogev-Falach et al. (2003) Amyloid Processing and Signal Transduction Properties of Antiparkinson-Antialzheimer Neuroprotective Drugs Rasagiline and TV3326. Annals of the New York Academy of Sciences 993: 378-386). Recent evidence from a delayed-start design study in Parkinson's Disease has suggested potential disease-modifying efficacy of rasagiline also in a clinical setting (Parkinson Study, G, A controlled, randomized, delayed-start study of rasagiline in early Parkinson's disease, Arch. Neurol. (2004) 61 (4): 561-6).

Whether rasagiline has positive effects on the peripheral auditory system has not been heretofore investigated.

SUMMARY OF THE INVENTION

This subject invention provides a method of treating or inhibiting hearing loss in a mammalian subject, comprising administering to the subject an amount of R(+)-N-propargyl-1-aminoindan or pharmaceutically acceptable salt thereof effective to treat or inhibit the hearing loss in the subject.

This subject invention also provides a method of alleviating a symptom of hearing loss in a mammalian subject, comprising administering to the subject an amount of R(+)-N-propargyl-1-aminoindan or pharmaceutically acceptable salt thereof effective to alleviate the symptom of hearing loss in the subject.

This subject invention also provides a pharmaceutical composition for the use in the treatment, prevention, or alleviation of symptoms of hearing loss in a subject which comprises a therapeutically effective amount of R(+)-N-propargyl-1-aminoindan or pharmaceutically acceptable salt thereof and pharmaceutically acceptable carrier.

This subject invention also provides a use of R(+)-N-propargyl-1-aminoindan or pharmaceutically acceptable salt thereof for the manufacture of medicament for the treatment, prevention or alleviation of a symptom of hearing loss.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Rasagiline was added to the perfusion fluid from the $8^{th}$ fraction and was maintained until the end of the experiment. Ratio values of electrically evoked dopamine release ($FRS_2/FRS_1$) in the absence and the presence of different concentrations of Rasagiline are shown for comparison. Data presented are means±SEM.

Figure 3:
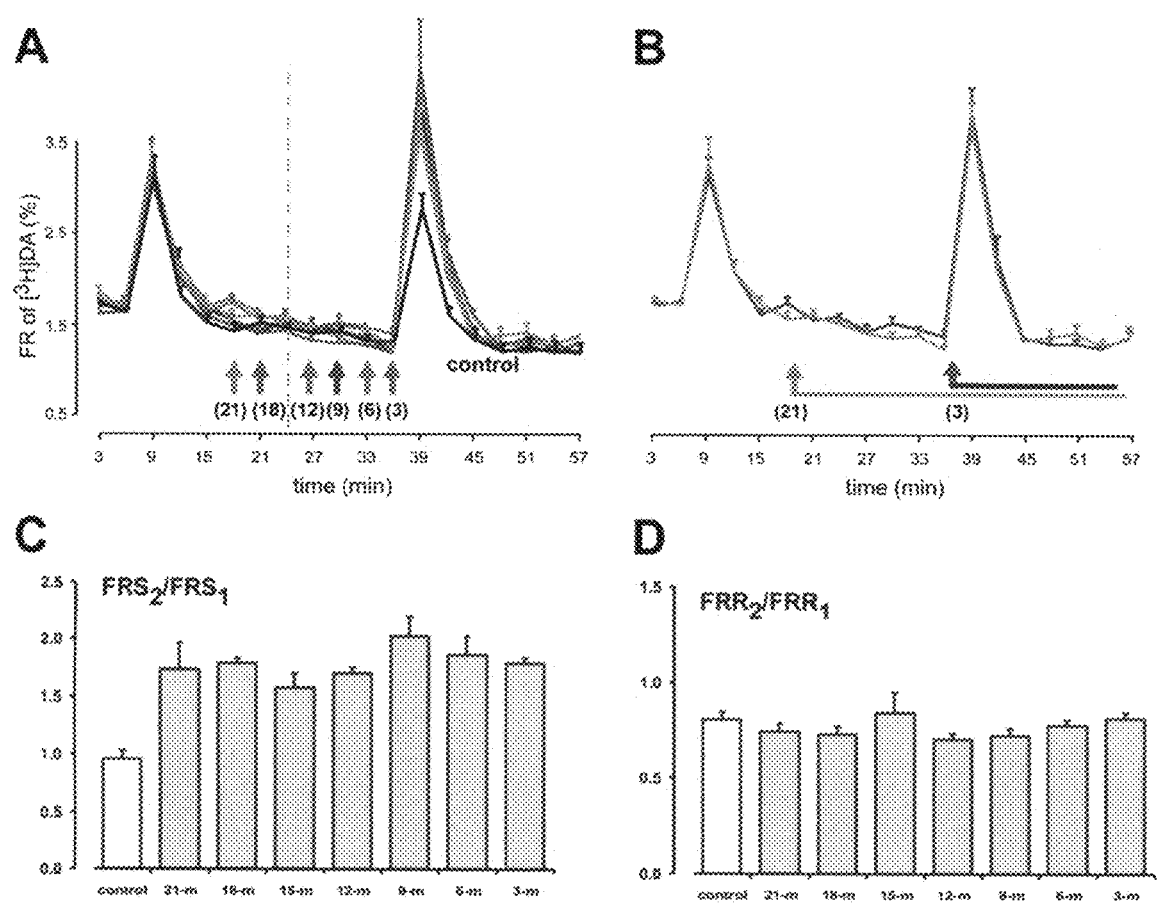

FIGS. 3A, B, C and D. shows the changes of duration of drug application did not influence the action of Rasagiline. (A) Time lapse changes in the release of dopamine from the cochlea in vitro. Rasagiline was added to the perfusion 3-21 minutes prior to the second electrical stimulation (in brackets). Dotted line indicates the timing of Rasagiline in our previous study ($8^{th}$ fraction, 15 min). (B) The shortest and the longest duration of Rasagiline perfusion are shown separately. (C) Ratio values of electrically evoked dopamine. (D) Ratio values of resting DA release. Data presented in C and D are means±SEM.

Figure 4:
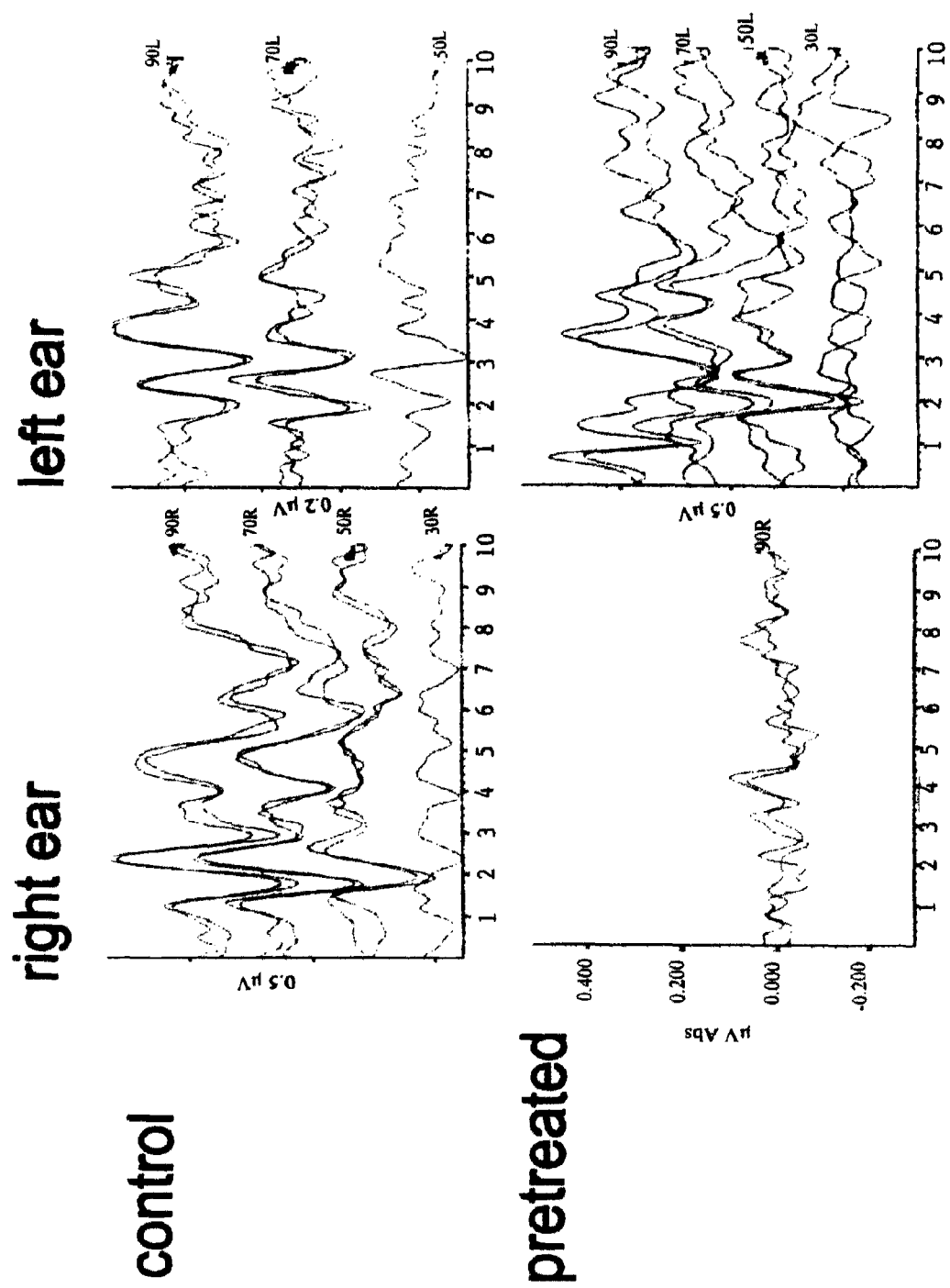

FIG. 4. shows an example for deafening the mouse ear with intratympanic application of neomycine recorded by auditory brainstem response (ABR) measurements in vivo. In the control measurement click stimuli evoked brainstem responses at normal hearing thresholds. After 3 weeks of intratympanic treatment with neomycine (pretreated) on the right and with saline on the left ear, no brainstem responses could be evoked in the ototoxic drug treated ear with the preservation of normal threshold on the other ear (vehicle control).

DETAILED DESCRIPTION OF THE INVENTION

The subject invention provides a method of treating or inhibiting hearing loss in a mammalian subject, comprising administering to the subject an amount of R(+)-N-propargyl-1-aminoindan or pharmaceutically acceptable salt thereof effective to treat or inhibit the hearing loss in the subject.

The subject invention also provides a method of alleviating a symptom of hearing loss in a mammalian subject, comprising administering to the subject an amount of R(+)-N-propargyl-1-aminoindan or pharmaceutically acceptable salt thereof effective to alleviate the symptom of hearing loss in the subject.

In an embodiment of the method the symptoms of hearing loss are selected from the group consisting of: muffled hearing, ringing, roaring, hissing, buzzing in the ear, ear pain, loss of hearing in one ear, plugged ear, otitis media and vertigo.

In another embodiment the hearing loss is induced by exposure to an ototoxic agent. The said ototoxic agent may be selected from the group consisting of antibiotics, chemotherapy, sound, environmental chemicals, loop diuretics, aspirin or quinine.

In another embodiment the mammalian subject is a human.

In the methods the amount of R(+)-N-propargyl-1-aminoindan or pharmaceutically acceptable salt thereof administered may be from 0.1 mg to 50.0 mg based on the weight of the R(+)-N-propargyl-1-aminoindan free base. The administration may be of the pharmaceutically acceptable salt of R(+)-N-propargyl-1-aminoindan. The pharmaceutically acceptable salt may be esylate, mesylate, sulfate, tannate or tartrate salt of R(+)-N-propargyl-1-aminoindan.

In the methods the administration is otic, oral, intraperitoneal, topical, parenteral or nasal administration. In an embodiment the administration may be topical otic application to the middle ear.

In another embodiment R(+)-N-propargyl-1-aminoindan or pharmaceutically acceptable salt thereof is crystalline.

In another embodiment the R(+)-N-propargyl-1-aminoindan or pharmaceutically acceptable salt thereof is in the form of a pharmaceutical composition. The pharmaceutical composition may be in tablet form.

In another embodiment of the method the pharmaceutical composition is in a form suitable for transdermal administration.

In another embodiment of the method the pharmaceutical composition is in a form suitable for sublingual administration.

The subject invention also provides a pharmaceutical composition for the use in the treatment, prevention, or alleviation of symptoms of hearing loss in a subject which comprises a therapeutically effective amount of R(+)-N-propargyl-1-aminoindan or pharmaceutically acceptable salt thereof and pharmaceutically acceptable carrier.

The subject invention also provides use of R(+)-N-propargyl-1-aminoindan or pharmaceutically acceptable salt thereof for the manufacture of medicament for the treatment, prevention or alleviation of a symptom of hearing loss.

Abbreviations
ABR—auditory brainstem response
AMPA—alpha-amino-3-hydroxy-5-methyl-4-isoxazole propionic acid
DA—dopamine
GADPH—glyceraldehyde-3-phosphate dehydrogenase
HEPES—4-(2-hydroxyethyl)-1-piperazineethanesulfonic acid
IHC—inner hair cells
HSD—highly significant differences
LOC—lateral olivocochlear
6-OHDA—6-hydroxydopamine
MPTP—1-methyl-4-phenyl-1,2,3,6-tetrahydropyridine
NMDA—N-methyl-D-aspartic acid
PARP—poly ADP ribose polymerase R(+)PAI mesylate is commercially available as Azilect® from Teva Pharmaceutical Industries Ltd. and Lundbeck A/S. R(+)PAI may be obtained by optical resolution of racemic mixtures of R- and S-enantiomers of PAI. Such a resolution can be accomplished by any conventional resolution method well known to a person skilled in the art. For example, the resolution may be carried out by preparative column chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired R enantiomer. A complete description of the preparation of R(+)PAI and its salts is described in U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514. The R(+)PAI salts include mesylate, maleate, fumarate, tartrate, hydrochloride, hydrobromide, esylate, p-toluenesulfonate, benzoate, acetate, phosphate, tannate and sulfate. For example, rasagiline tannate may be prepared by a process comprising combining a solution of tannic acid with rasagiline base.

As used herein, the term "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. For example, an amount effective to inhibit, attenuate or reverse hearing loss symptoms. The specific effective amount may vary with such factors as the particular condition being treated, the physical condition of the patient, the type of mammal being treated, the duration of the treatment, the nature of concurrent therapy (if any), and the specific formulations employed and the structure of the compounds or its derivatives.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds may comprise a single compound or mixtures thereof with hearing loss compounds or with other compounds also used to treat neurite damage. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the cancer, all using dosage forms well known to those of ordinary skill in the pharmaceutical arts.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

In development of pharmaceutical compositions, crystallinity is a desirable property in an active pharmaceutical ingredient. Crystal substances allow for ease in processing and formulating into most types of pharmaceutical dosage forms.

By any range disclosed herein, it is meant that all hundredth, tenth and integer unit amounts within the range are specifically disclosed as part of the invention. Thus, for example, 0.01-50.0 mg means that 0.02, 0.03 . . . 0.09; 0.1, 0.2 . . . 0.9; and 1, 2 . . . 49 mg unit amounts are included as embodiments of this invention.

As used herein, a subject "afflicted" with hearing loss means the subject has been diagnosed with hearing loss or a condition wherein hearing loss can occur.

In this application, a subject diagnosed with hearing loss refers to a subject diagnosed with hearing impairments attributed to a wide variety of causes, including infections, mechanical injury, loud sounds, aging, and chemically induced ototoxicity that damages neurons and/or hair cells of the peripheral auditory system. Symptoms include muffled hearing, ringing, roaring, hissing, buzzing in the ear, ear pain, loss of hearing in one ear, plugged ear otitis media and vertigo. Diagnosis may be by hearing by air conduction, hearing by bone conduction, Rinne's test, audiometry, speech audiometry, speech discrimination, tympanometry, or acoustic reflex testing. Rasagiline may be used as a potential therapeutic prevent or inhibit hearing loss.

This invention will be better understood from the experimental details which follow. However, one skilled in the art will readily appreciate that the specific methods and results discussed are merely illustrative of the invention as described more fully in the claims which follow thereafter.

Discussion

Dopamine (DA) was identified as a possible modulator of the IHC-afferent synapse (Safieddine S, Prior A M, Eybalin M, (1997) Choline acetyltransferase, glutamate decarboxylase thyrosine hydroxilase, calcitonin gene-related peptide and opioid peptides coexist in lateral efferent neurons of rat and guinea-pig. Eur J Neurosci 9: 356-367). It is well known that the cochlea is vulnerable to different noxae that can lead to sensorineural hearing loss (Pujol R, Puel J-L, (1999) Excitotoxicity, synaptic repair, and functional recovery in the mammalian cochlea: a review of recent findings. Ann NY Acad Sci 884: 249-54). In addition to the dysfunction of the supplier arteries other pathological noxae (like endolymphatic hydrops or noise trauma) can cause ischemia in the organ of Corti (Vass Z, Brechtelsbauer P B, Nuttall A L, Miller J M, (1995) Effect of endolympahtic hydrops on capsaicin evoked increase in cochlear blood flow. Acta Otolaryngol 115: 754-758). Excitotoxicity is also playing a role in the pathomechanisms of presbyacusis (Seidman M D, Quirk W S, Shirwany N A, (1999) Mechanisms of alterations in the microcirculation of the cochlea. Ann NY Acad Sci 884: 226-232), aminoglycoside-induced ototoxicity (Duan M, Agerman K, Ernfors P, Canlon B, (2000) Complementary roles of neurotrophin 3 and a N-methyl-D-aspartate antagonist in the protection of noise and aminoglycoside-induced ototoxicity. Proc Natl Acad Sci USA 97: 7597-7602) and tinnitus (Sahley T L, Nodar R H, (2001) A biochemical model of peripheral tinnitus. Hear Res 152: 43-54).

Harmful stimuli also activate the cochlear nuclei, which can release protective transmitters in the cochlea: the dopamine-containing LOC efferent fibers were shown to establish a short-loop feedback mechanism between the brainstem and the cochlea (Pujol R, (1994) Lateral and medial efferents: a double neurochemical mechanism to protect and regulate inner and outer hair cell function in the cochlea. Br J Audiol 28: 185-191). In line with the theory of the cochleo-protective role of the LOC substance dopamine, (i) $D_1$ and $D_2$ receptor agonists inhibited the NMDA(N-methyl-D-aspartic acid)- and AMPA(alpha-amino-3-hydroxy-5-methyl-4-isoxazole propionic acid)-induced firing of the primary afferent nerve (Puel J-L, Bobbin R P, Fallon M, (1988) An ipsilateral cochlear efferent loop protects the cochlea during intense sound exposure. Hear Res 37: 65-70), (ii) stimulation of the LOC fibers decreased the amplitude of the cochlear compound action potential evoked by intensive sound stimulation (Oestreicher E, Arnold W, Ehrenberger K, Felix D, (1997) Dopamine regulates the glutamatergic inner hair cell activity in guinea pigs. Hear Res 107: 46-52), and finally (iii) intracochlear application of the $D_2/D_3$ dopamine receptor agonist piribedil reduced the characteristic electrophysiological and structural changes evoked by ischemia (d'Aldin C, Eybalin M, Puel J-L, Characon G, Ladrech S, Renard N, Pujol R, (1995a) Synaptic connections and putative functions of the dopaminergic innrevation of the guinea pig cochlea. Eur Arch Otorhinolar 252: 270-274. d'Aldin C, Puel J-L, Leducq R, Crambes O, Eybalin M, Pujol R, (1995b) Effect of a dopaminerg agonist in the guinea pig cochlea. Hear Res 90: 202-211; Gil-Loyzaga P, (1995) Neurotransmitters of the olivocochlear lateral efferent system: with an emphasis on dopamine. Acta Otolaryngol 115: 222-226; Pujol R, Puel J-L, d'Aldin C G, Eybalin M, (1993) Pathophysiology of the glutamergic synapses in the cochlea. Acta Otolaryngol. 113: 330-334). In addition, it has been shown that experimental ischemia and activation of the known neuroprotective metabotropic glutamate receptors can induce in vitro dopamine release from the acutely isolated cochlea (Halmos G, Doleviczenyi Z, Vizi E S, Lendvai B. Zelles T. (2005) Oxygen-glucose deprivation evokes dopamine release in isolated cochleae. Neuroscience 132: 801-809, Doleviczenyi Z, Halmos G, Repassy G, Vizi E S, Zelles T, Lendvai B., (2005) Cochlear dopamine release is modulated by group II metabotropic glutamate receptors via GABAergic neurotransmission. Neurosci. Lett. 385: 93-98). Taken together, these data sufficiently established the potential neuroprotective effect of dopamine during ischemia.

The present invention describes the modulation of dopamine release by rasagiline to evoke this protective factor in ischemia. Rasagiline, at the applied concentrations and timing, can cause an enhancement of the field stimulation-evoked dopamine release as revealed by the $FRS_2/FRS_1$ values in the cochlea preparation. The increase was significant at the higher concentrations, 100 and 300 µM of Rasagiline.

EXAMPLES

Example 1

Animals and Tissue Preparation

The bulla tympani of a male guinea pig (weighing 150-350 g) was opened. The bony capsule of the cochlea was removed under stereomicroscopic guidance and the stria vascularis was stripped and the cochlea was fractured at the basis of the modiolus. The preparation contained the ganglion spirale, the afferent auditory fibers, the axons and axon terminals of the efferent bundles and both the inner and outer hair cells. All experiments were carried out in a perilimph-like solution, which contained 150 nM NaCl, 3.5 mM KCl, 1 mM $CaCl_2$, 1 mM $MgCl_2$, 2.75 mM HEPES and 2.25 mM Tris-OH at the temperature of 37° C. and pH 7.4. The osmolality was set by D-glucose and continuously saturated by 100% $O_2$.

Microvolume Superfusion

The cochleae were incubated with 0.2 µM [3H]dopamine (Amersham, UK, spec. act.: 31.0 Ci/mmol, 6 µCi in 1 ml) for 35 min. Each cochlea was then placed in a microvolume plexi chamber and superfused at 3 ml/min with perilymph-like solution. After 1 hour pre-perfusion the outflow was collected into 3 min-fractions. The released activity was determined by assaying 500 ml-aliquots of each sample with liquid scintillation spectrometry (Packard Tri-Carb 1900TR). After collecting samples for 57 minutes (19 fractions) each cochlea was transferred from the microchambers to 500 µl of 10% trichloroacetic acid for one day and 100 µl was assayed for tissue radioactivity. Earlier HPLC measurements showed that 91-95% of the stimulation-evoked radioactivity could be attributable to [$^3$H]dopamine and its metabolites (Gáborján A, Lendvai B, Vizi E S, (1999a) Neurochemical evidence of dopamine release by lateral olivocochlear efferents and its presynaptic modulation in guinea-pig cochlea. Neuroscience 90: 131-138). Electrical field stimulation was applied for one fraction period (3 min, 360 pulses) at 60 V, 2 Hz and 0.5 ms duration at the $3^{rd}$ and $13^{th}$ fractions. The pulses were delivered by a Grass S88 stimulator (West Warwick, USA) through platinum electrodes at the top and bottom of the tissue chamber.

Concentration Dependence

Figure 1:
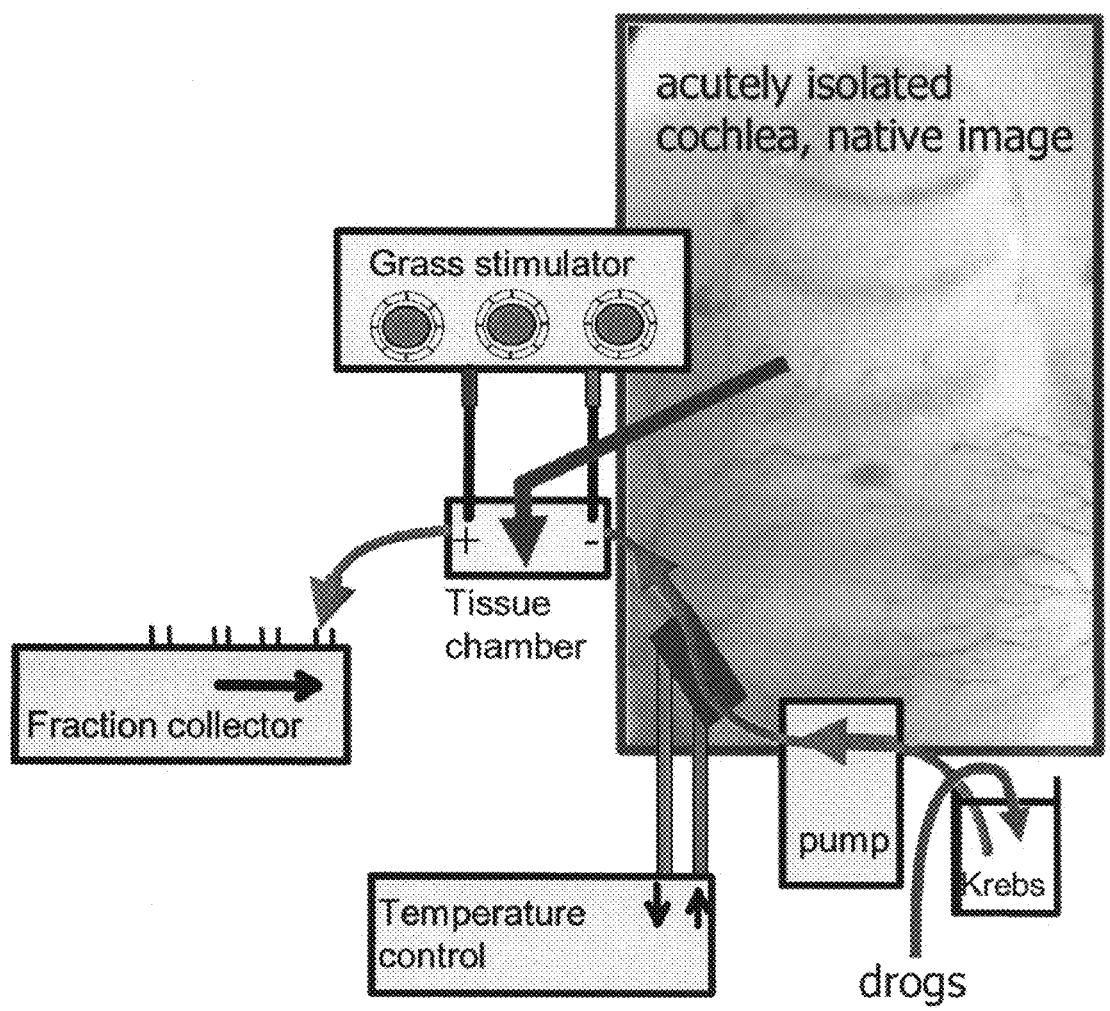
FIG. 1. shows a schematic drawing of the experimental design.
Figure 2:
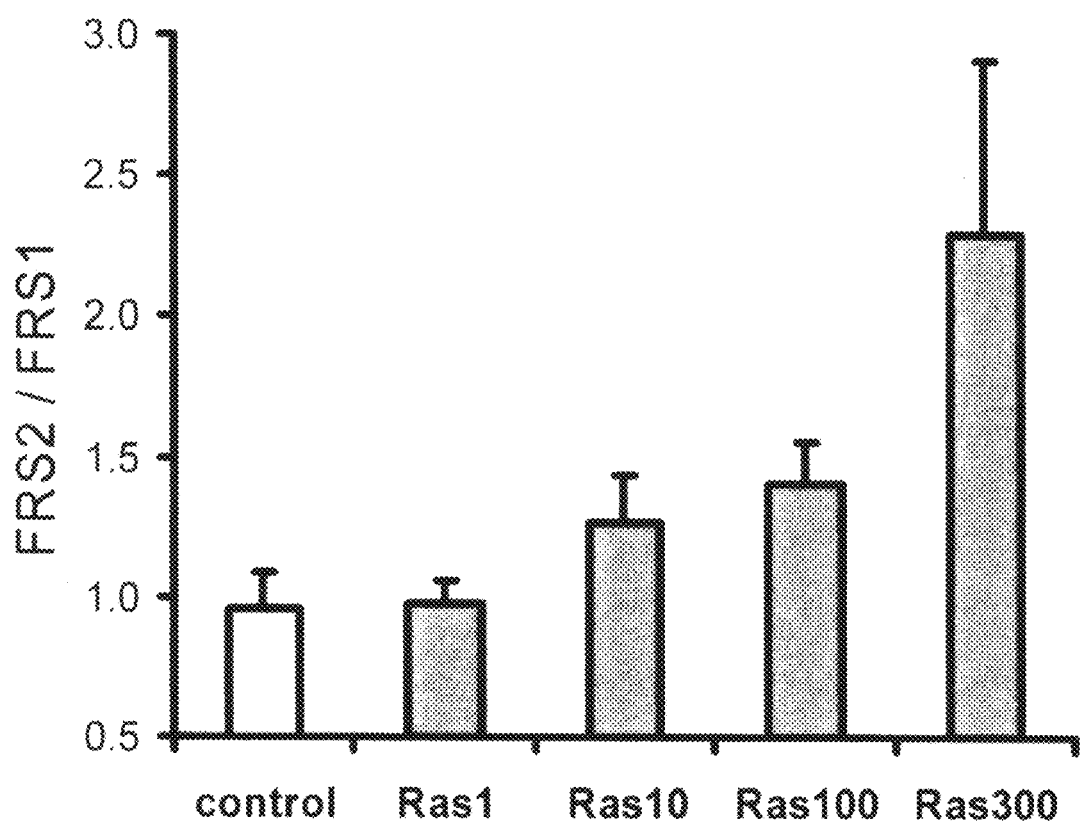
FIG. 2. shows the effect of the Rasagiline on dopamine release from the guinea pig cochlea preparation was concentration dependent.

Rasagiline was added to the perfusion fluid, 15 minutes prior to the second field stimulation ($8^{th}$ fraction) at the concentration of 1, 10, 100 and 300 µM and maintained until the end of the experiments. At the low concentration, Rasagiline did not change cochlear dopamine release while higher doses elevate cochlear DA release (FIG. 2).

Effect of Timing of Rasagiline Application on the Evoked Cochlear Dopamine Release The examination of the timing effect of Rasagiline perfusion came to address the possible involvement of slow intracellular processes in the action of Rasagiline in the cochlea, such as interaction with phosphorylation of intracellular enzymes or receptors or interference with protein synthesis. The assumption was that the longer the time before the second electrical stimulation, the larger the effect on the amplitude of the evoked dopamine release. In these experiments Rasagiline (100 µM) was added to the perfusion 21, 18, 12, 9, 6, and 3 minutes prior to the second field stimulation.

The different timing of Rasagiline perfusion did not cause different enhancement of the evoked dopamine release (FIG. 3A-C). Furthermore, Rasagiline given even at the longest duration (21 minutes prior to stimulation) failed to induce significant differences in the resting release of dopamine (FIGS. 3B, D).

All groups with the various timing of Rasagiline perfusion caused a significant enhancement of evoked dopamine release (Table 1). In contrast, the p-values of post hoc test revealed no further differences between timing groups. Numbers as presented in the table are probability (p) values of Tukey HSD post hoc comparisons (a statistical method used for testing the statistical significance of unplanned pair wise comparisons, Winer, Michels & Brown, 1991) between treatment groups of 3, 6, 9, 12, 18, 21 minutes perfusion with Rasagiline and a control. Significant p-values are indicated by underline.

TABLE 1 p-values of Rasagiline timing experiments showing significant enhancement of dopamine release.

|  | 3-min | 6-min | 9-min | 12-min | 18-min | 21-min |
|---|---|---|---|---|---|---|
| 6-min | 0.999763 | | | | | |
| 9-min | 0.867797 | 0.975706 | | | | |
| 12-min | 0.998655 | 0.970966 | 0.535902 | | | |
| 18-min | 1.000000 | 0.999780 | 0.887884 | 0.999156 | | |
| 21-min | 0.999926 | 0.992801 | 0.699156 | 0.999996 | 0.999957 | |
| control | <u>0.006352</u> | <u>0.002175</u> | <u>0.000205</u> | <u>0.016949</u> | <u>0.011157</u> | <u>0.014986</u> |

Data Analysis

To best describe the release of dopamine during one collecting period, the fractional release (FR) of the tritium-outflow was determined as the percentage of total radioactivity present in the tissue at the time of sample collection. The fractional release evoked by field stimulations ($S_1$ and $S_2$) was calculated by the area-under-the-curve, i.e., by subtracting the mean of the basal release from the total fractional release during the electrical stimulation (Halmos G, Gáborján A, Lendvai B, Répássy G, Z Szabó L, Vizi E S, (2000) Veratridine-evoked release of dopamine from guinea pig isolated cochlea. Hear Res 144: 89-96, Halmos G, Lendvai B, Gáborján A, Baranyi M, Z Szabó L, Csokonai Vitéz L, (2002) Simultaneous measurement of glutamate and dopamine release from isolated guinea pig cochlea. Neurochem Int 40: 243-248). The effects of drugs on the field stimulation-evoked [$^3$H]dopamine release were expressed by the calculated ratio of $FRS_2$ over $FRS_1$, in the presence and in the absence of the drug, respectively. The effect of drugs on the resting outflow of tritium was determined as the ratio of the sum of the two highest consecutive resting FR values in the presence of the drug and before the drug reached the cochleae ($FRR_2/FRR_1$). Data are expressed as the means±S.E.M. ANOVA was used for statistical analysis. Tukey post-hoc test was applied to determine the significance of pair wise comparisons.

Example 2

In Vivo Auditory Brainstem Response (ABR) Measurements in Mice

Summary

Mice were treated with intratympanic neomycin (200 mg/ml) on the right ear on two consecutive days. Left ears were left for vehicle control (NaCl injection). In order to develop significant hearing loss, the measurement of brainstem evoked potentials were made 3 weeks after the pretreatment with neomycin (under general anaesthesia). Click stimulations to the ear including various frequencies were used to evoke the auditory response in the brainstem that was measured by multiple electrodes placed on the head of the animal.

Discussion:

Control experiments showed the hearing threshold of each ear (FIG. 4). Pretreatment with the known ototoxic neomycin produced evident hearing loss in the treated side (FIG. 4). Hearing impairment was not due to the intervention itself because the vehicle-treated side showed no hearing deficit (FIG. 4).

Next, the potential protective role of Rasagiline on neomycin-induced hearing loss in vivo was evaluated. The examination of the anticipated protective effect of Rasagiline took place in two sets of experiments. In the first experiment, Rasagiline was applied topically in the middle ear, by injecting 0.5 mg Rasagiline intratympanically together with neomycine one time (0.5 mg/day) (n=4). Rasagiline completely inhibited the ototoxic effect of neomycine in this series of experiments; the hearing threshold of the intratympanically treated animals remained unchanged compared to the threshold prior to the neomycine treatment. In the second experiment the effect of systemic application of Rasagiline was studied. Rasagiline (100 µL) was applied intraperitoneally on the day of intratympanic neomycine treatment and the next three days (50 mg/kg Rasagiline daily) (n=4). In contrast to the topical application, the systemic use of Rasagiline could not prevent the ototoxic effect of the aminoglicoside drug. All neomycine treated ears became deaf.

Intratympanic application of Rasagiline have neuroprotective effect against aminoglicoside ototoxicity indicating the potential therapeutic use of Rasagiline to prevent hearing loss.

Example 3

In Vivo Auditory Brainstem Response (ABR) Measurements in Guinea Pigs

Animals

Guinea pigs weighing 250-300 g were used in all experiments. All interventions (including ABR measurements and intratympanic treatments) are performed under general anesthesia using i.p. injection of a cocktail of Ketamine and Xylazine.

ABR Measurement

A loudspeaker is placed in each ear and the ABR responses were detected by four surface electrodes. These electrodes are placed two in the mastoid region and one in vertex as positive and fourth electrode was placed on forehead as the ground electrode. Calibrated acoustic signals are obtained to evoke brainstem response. The visual detection threshold is determined by decrement sound pressure in 5 dB steps. The evoked responses are then filtered and averaged with 500 sweeps using a signal processor. All ABR tests are performed bilaterally and baseline Peak Equivalent Sound Pressure Levels (PESPLs) are obtained in terms of decibel (dB). All animals undergo baseline hearing test (ABR) before any kind of treatment in order to rule out previous hearing loss. Control ABR threshold measurements are compared to pretreatment values. Auditory threshold shift is subjected to statistical analysis, statistical significance is determined.

Study Groups

All treatment group contain the intratympanic application of neomycin and performed under stereomicroscopic guidance. A fine needle is used for myringotomy and drugs are delivered through the same needle. The whole middle ear is filled until the fluid can be seen in the external auditory canal. Animals are laid on the opposite side for 5 min after intratympanic injection in order to avoid the leakage of drugs from the middle ear. Typical injections are approximately 100 ml of solution into the middle ear to avoid spillover at larger volumes. Concentration is calculated using this volume. For example, a 50 mg/kg Rasagiline dose for a 300 g guinea pig is achieved by giving 15 mg Rasagiline dissolved in 100 ml solution. After the baseline threshold measurement animals are divided into different treatment groups as follows:

Control group: Right ear: neomycin 1 mg/kg, left ear: vehicle, n=6 animals;

Rasagiline IP study group: N=6-8 animals, three days before intratympanic neomycin treatment: Rasagiline 1 mg/kg day; Intratympanic neomycine (1 mg/kg) in both ears.

After the intratympanic neomycine application: Rasagiline 1 mg/kg day intraperitoneally or per os for 3 weeks (during the whole duration of ABR measurement). Rasagiline intratympanic effect study group. N=6 animals right ear: Neomycine 1 mg/kg and Rasagiline, 50 mg/kg, left ear: Neomycin only 1 mg/kg. Intratympanic application only to assess the effect of local Rasagiline administration (same design as in the preliminary experiment).

To estimate the threshold of hearing the sound stimulus is applied at different frequencies. In control animals at a particular frequency the sound induces a response in the ear. In deaf animals response is usually not detected at any frequency.

Discussion:

Control experiments show the hearing threshold of each ear. Pretreatment with the known ototoxic neomycin produces evident hearing loss in the treated side. Hearing impairment is not due to the intervention itself because the vehicle-treated side shows no hearing deficit.

Next, the potential protective role of Rasagiline on neomycin-induced hearing loss in vivo is evaluated. The examination of the anticipated protective effect of Rasagiline takes place in two sets of experiments. In the first experiment, Rasagiline is applied topically in the middle ear, by injecting 0.5 mg Rasagiline intratympanically together with neomycine one time. Rasagiline completely inhibits the ototoxic effect of neomycine in this series of experiments; the hearing threshold of the intratympanically treated animals remains unchanged compared to the threshold prior to the neomycine treatment. In the second experiment the effect of systemic application of Rasagiline is studied. Rasagiline is applied intraperitoneally on the day of intratympanic neomycine treatment and the next three days. In contrast to the topical application, the systemic use of Rasagiline can not prevent the ototoxic effect of the aminoglicoside drug. All neomycine treated ears become deaf.

Intratympanic application of Rasagiline has a neuroprotective effect against aminoglicoside ototoxicity indicating the potential therapeutic use of Rasagiline to prevent hearing loss.

The invention claimed is:

1. A method of treating or inhibiting hearing loss in a mammalian subject, comprising administering to the subject an amount of R(+)-N-propargyl-1-aminoindan or pharmaceutically acceptable salt thereof effective to treat or inhibit the hearing loss in the subject, wherein the hearing loss is induced by exposure to an ototoxic agent.

2. A method of alleviating a symptom of hearing loss in a mammalian subject, comprising administering to the subject an amount of R(+)-N-propargyl-1-aminoindan or pharmaceutically acceptable salt thereof effective to alleviate the symptom of hearing loss in the subject, wherein the hearing loss is induced by exposure to an ototoxic agent.

3. The method of claim 2, wherein the symptoms of hearing loss are selected from the group consisting of: muffled hearing, ringing, roaring, hissing, buzzing in the ear, ear pain, loss of hearing in one ear, plugged ear, otitis media and vertigo.

4. The method of claim 1, wherein said ototoxic agent is antibiotics, chemotherapy, sound, environmental chemicals, loop diuretics, aspirin or quinine.

5. The method of claim 1, wherein the mammalian subject is a human.

6. The method of claim 1, wherein the amount of R(+)-N-propargyl-1-aminoindan or pharmaceutically acceptable salt thereof administered is from 0.1 mg to 50.0 mg based on the weight of the R(+)-N-propargyl-1-aminoindan free base.

7. The method of claim 6, wherein the amount of R(+)-N-propargyl-1-aminoindan or pharmaceutically acceptable salt thereof administered is from 0.1 mg to 10.0 mg based on the weight of R(+)-N-propargyl-1-aminoindan free base.

8. The method of claim 1, wherein the administration is of the pharmaceutically acceptable salt of R(+)-N-propargyl-1-aminoindan.

9. The method of claim 8, wherein the pharmaceutically acceptable salt is esylate, mesylate, sulfate, tannate or tartrate salt of R(+)-N-propargyl-1-aminoindan.

10. The method of claim 8, wherein the pharmaceutically acceptable salt is the mesylate salt of R(+)-N-propargyl-1-aminoindan.

11. The method of claim 1, wherein the administration is otic, oral, intraperitoneal, topical, parenteral or nasal administration.

12. The method of claim 11, wherein the administration is topical otic application to the middle ear.

13. The method of claim 1 wherein R(+)-N-propargyl-1-aminoindan or pharmaceutically acceptable salt is crystalline.

14. The method of claim 1 wherein the R(+)-N-propargyl-1-aminoindan or pharmaceutically acceptable salt thereof is in the form of a pharmaceutical composition.

15. The method of claim 14, wherein the pharmaceutical composition is in tablet form.

16. The method of claim 14 wherein the pharmaceutical composition is in a form suitable for transdermal administration.

17. The method of claim 14 wherein the pharmaceutical composition is in a form suitable for sublingual administration.

* * * * *